United States Patent
Cohen et al.

(10) Patent No.: US 11,039,954 B2
(45) Date of Patent: Jun. 22, 2021

(54) IMPLANTABLE OCULAR DRUG DELIVERY DEVICES AND METHODS

(71) Applicant: MicroOptx Inc., Maple Grove, MN (US)

(72) Inventors: Edward Aaron Cohen, Columbia Heights, MN (US); Daniel Charles Voce, Princeton, MN (US)

(73) Assignee: MicroOptx Inc., Maple Grove, MN (US)

( * ) Notice: Subject to any disclaimer, the term of this patent is extended or adjusted under 35 U.S.C. 154(b) by 0 days.

(21) Appl. No.: 16/360,777

(22) Filed: Mar. 21, 2019

(65) Prior Publication Data

US 2020/0297530 A1    Sep. 24, 2020

(51) Int. Cl.
| | | |
|---|---|---|
| *A61F 9/00* | (2006.01) | |
| *A61F 9/007* | (2006.01) | |
| *A61K 31/573* | (2006.01) | |
| *A61K 9/00* | (2006.01) | |
| *A61M 31/00* | (2006.01) | |
| *A61K 9/16* | (2006.01) | |

(52) U.S. Cl.
CPC ........ *A61F 9/0017* (2013.01); *A61F 9/00781* (2013.01); *A61K 9/0051* (2013.01); *A61K 31/573* (2013.01); *A61F 2250/0067* (2013.01); *A61K 9/0004* (2013.01); *A61K 9/0024* (2013.01); *A61K 9/1647* (2013.01); *A61M 31/002* (2013.01)

(58) Field of Classification Search
CPC .... A61F 9/0017; A61F 9/0004; A61F 9/0024; A61F 9/00781; A61F 2250/0067; A61M 31/002; A61M 31/573
See application file for complete search history.

(56) References Cited

U.S. PATENT DOCUMENTS

| | | |
|---|---|---|
| 5,378,475 A | 1/1995 | Smith et al. |
| 6,217,895 B1 | 4/2001 | Guo et al. |
| 7,708,711 B2 | 5/2010 | Tu et al. |
| 8,007,459 B2 | 8/2011 | Haffner et al. |
| 8,529,492 B2 | 9/2013 | Clauson et al. |
| 8,574,659 B2 | 11/2013 | Guo et al. |
| 9,012,437 B2 | 4/2015 | Wong et al. |
| 9,192,511 B2 | 11/2015 | Shiah et al. |
| 2003/0229303 A1* | 12/2003 | Haffner ............... A61F 9/00781 604/8 |
| 2004/0127843 A1* | 7/2004 | Tu ........................ A61F 9/0017 604/27 |
| 2008/0132999 A1* | 6/2008 | Mericle .................... A61F 2/07 623/1.34 |
| 2011/0238075 A1* | 9/2011 | Clauson ............... A61K 9/0048 606/107 |
| 2014/0171885 A1 | 6/2014 | Clauson et al. |
| 2016/0354309 A1 | 12/2016 | Heitzmann et al. |

FOREIGN PATENT DOCUMENTS

WO    WO 2018/027009    2/2018

OTHER PUBLICATIONS

Krishnan et al; title: Advances in polymers for anti-biofouling surfaces; J. Mater. Chem., 2008, vol. 18, pp. 3405-3413. (Year: 2008).*
International Search Report & Written Opinion in International Application No. PCT/US2020/023919 dated Aug. 14, 2020, 11 pages.

* cited by examiner

*Primary Examiner* — Yanzhi Zhang
(74) *Attorney, Agent, or Firm* — Fish & Richardson P.C.

(57) ABSTRACT

An implantable ocular drug delivery system can include inserting an implantable device into an eye, where the device contains therapeutics intended to be released for local or systemic effects. In some implantable device embodiments, the device includes a microchannel intended to reduce intraocular pressure. In some implantable device embodiments, the device includes a microchannel intended to treat dry eye.

19 Claims, 9 Drawing Sheets

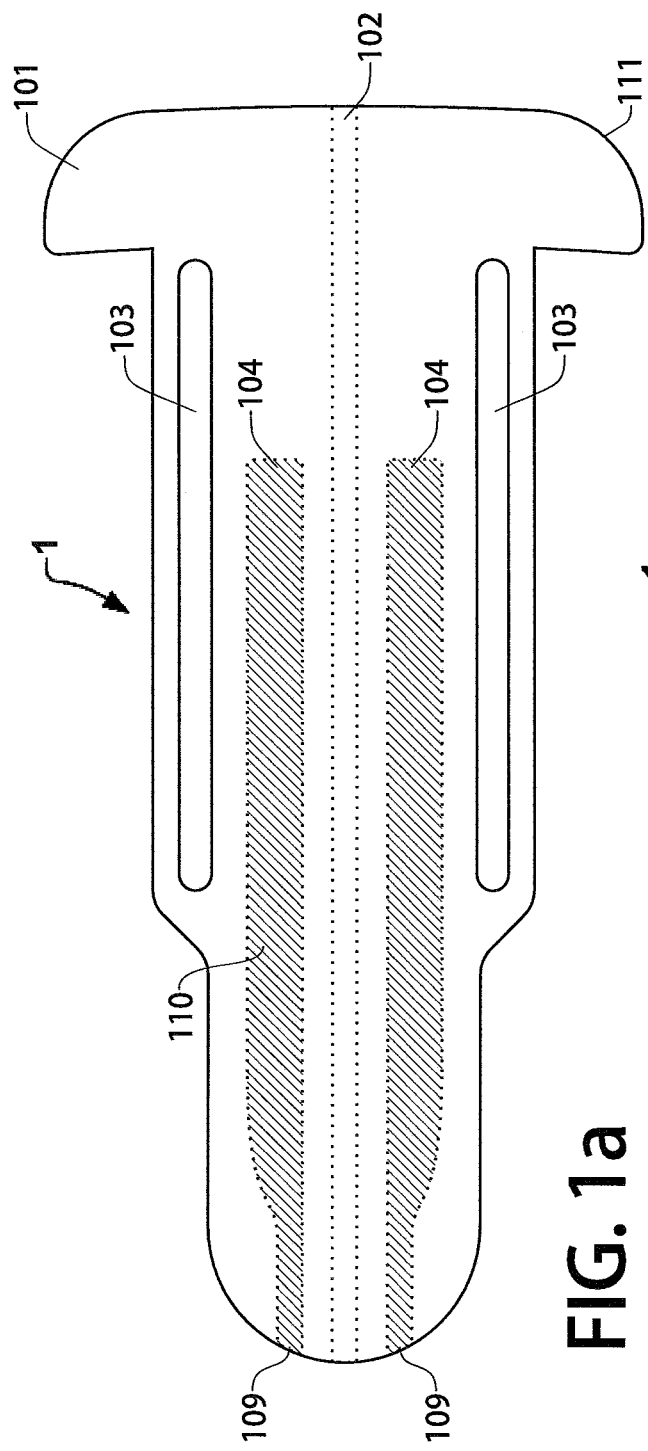
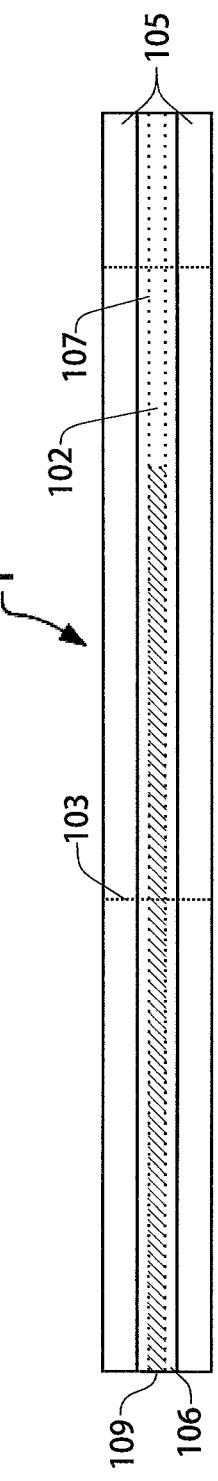
FIG. 1a
FIG. 1b

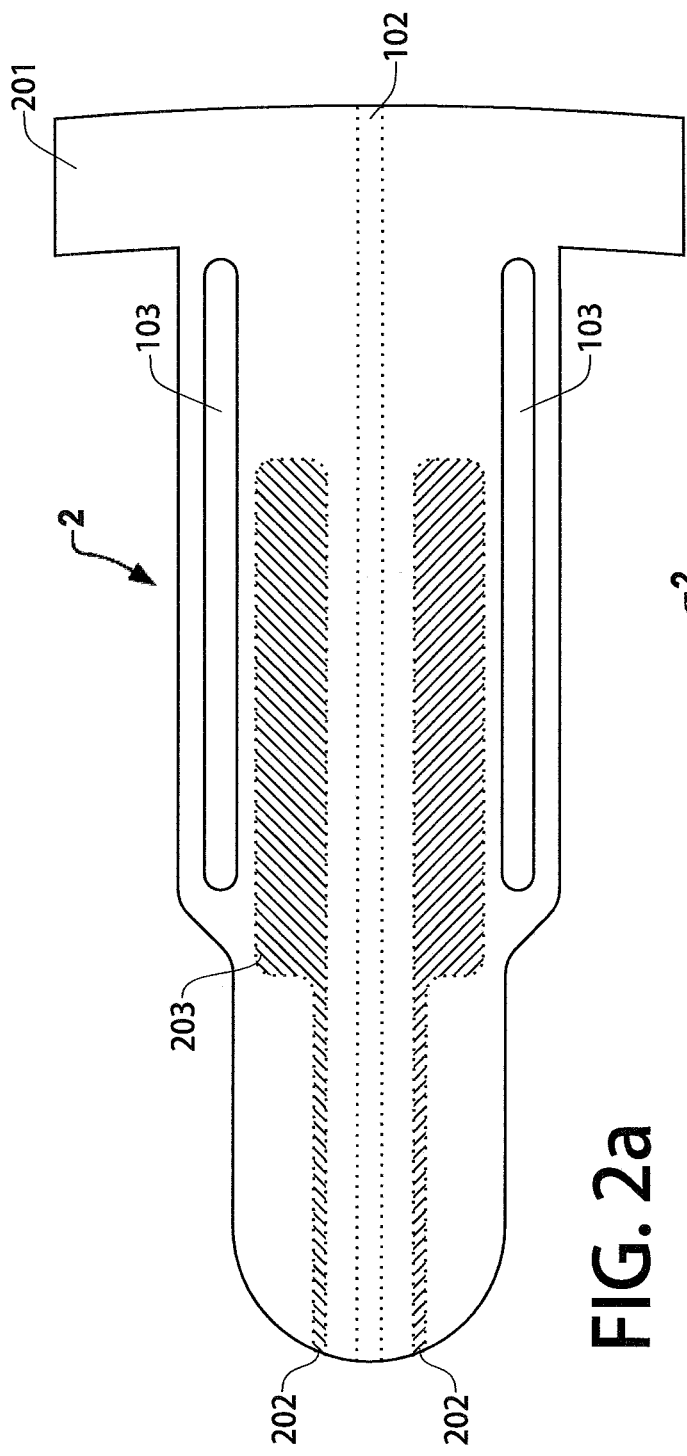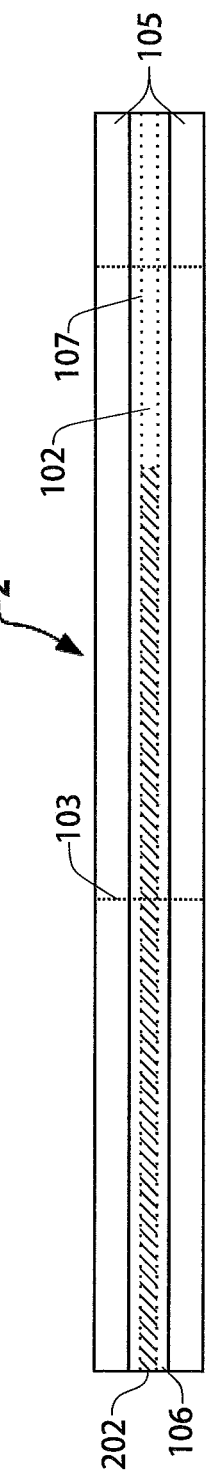
FIG. 2a
FIG. 2b

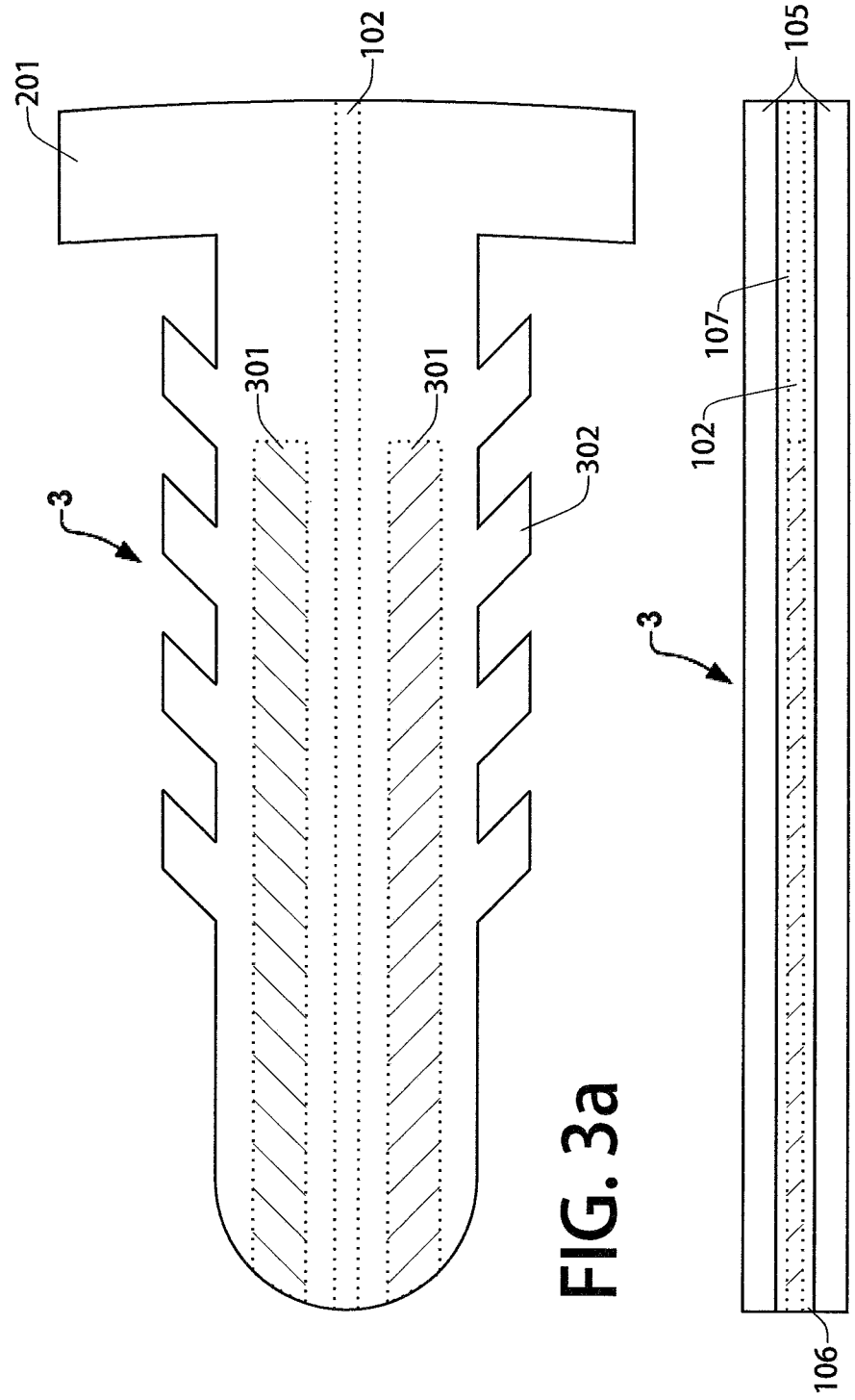

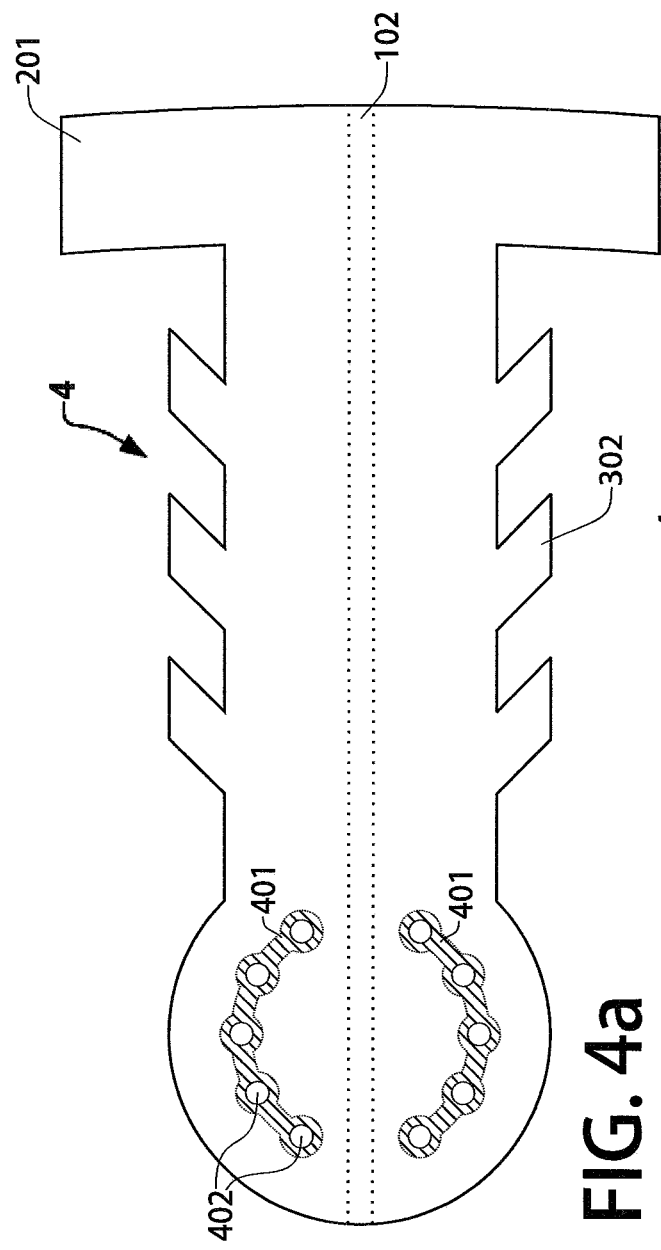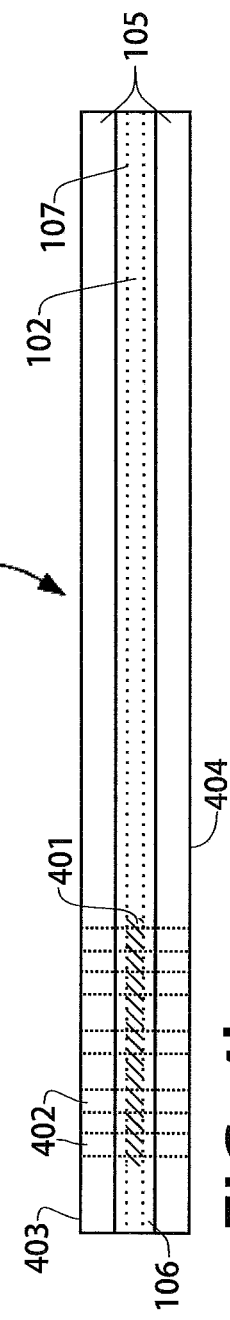
FIG. 4a
FIG. 4b

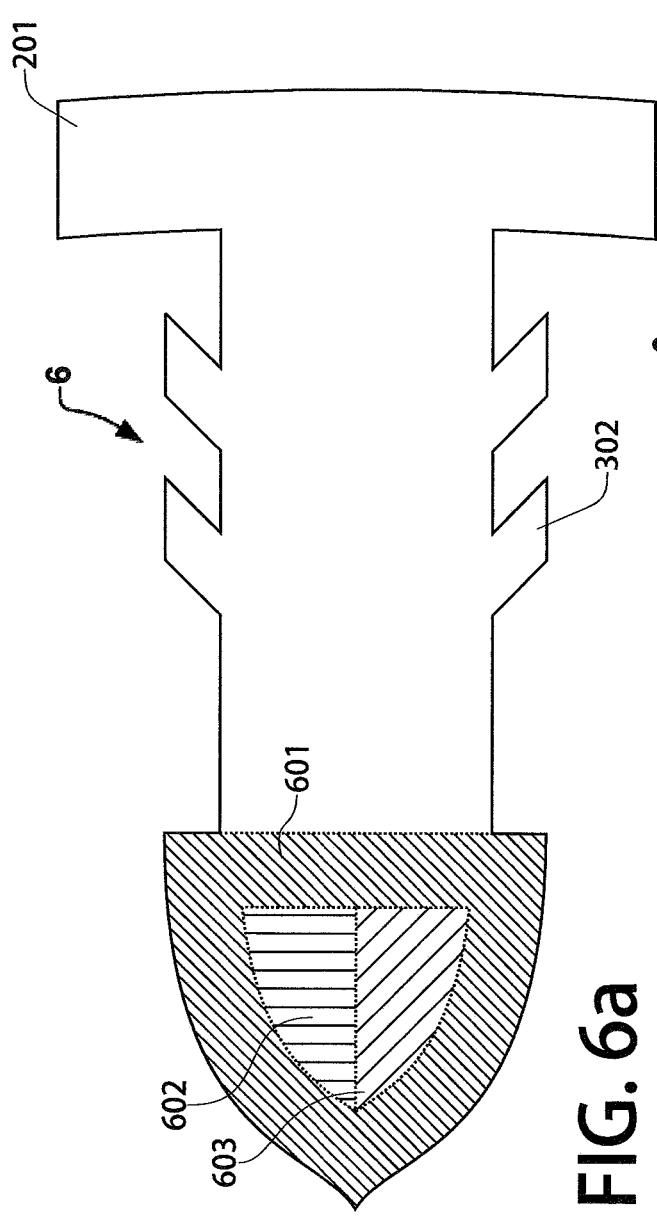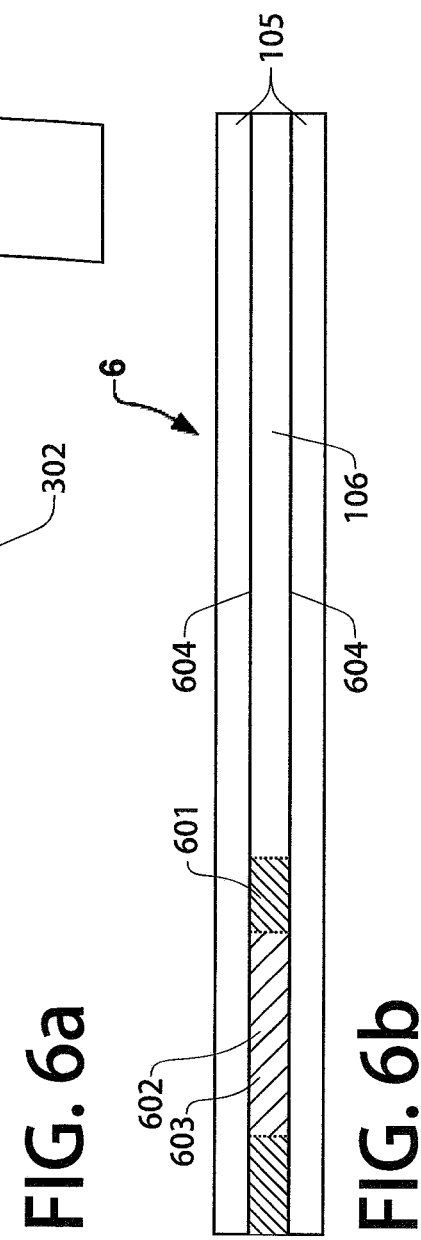

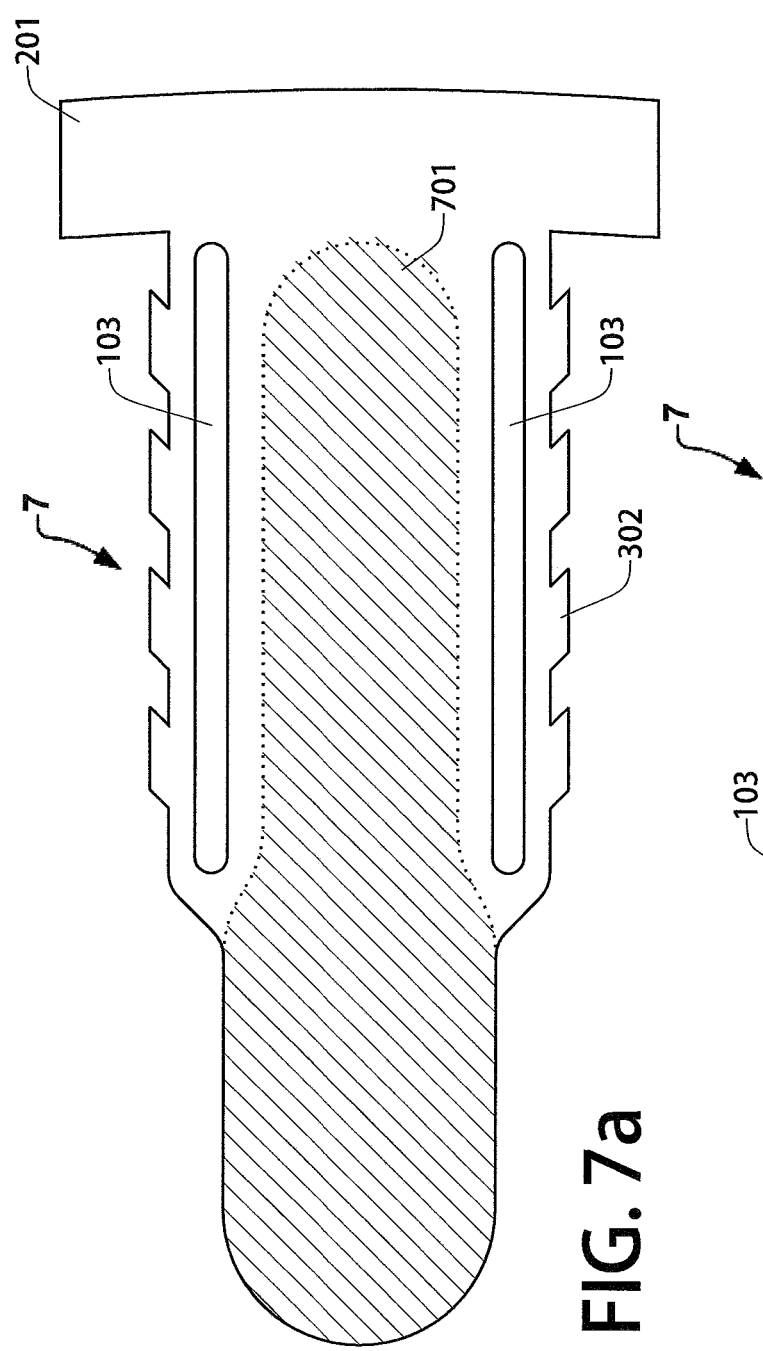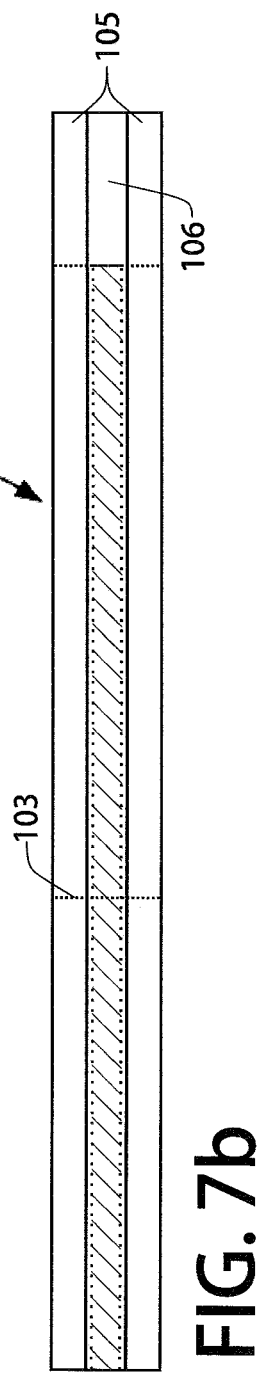
FIG. 7a
FIG. 7b

IMPLANTABLE OCULAR DRUG DELIVERY DEVICES AND METHODS

BACKGROUND

1. Technical Field

This document relates to devices for drug delivery. For example, this document relates to implantable ocular drug delivery devices that distribute drugs into the anterior chamber of the eye.

2. Background Information

Diseases of the eye are prevalent across the globe. In the United States alone, over 45 million Americans age 40 or older are affected by common eye diseases such as cataracts, glaucoma, diabetic retinopathy, age-related macular degeneration, dry eye, and severe infection. Those that cause blindness and irreversible vision loss cost nearly 50 billion dollars each year in the United States. Eye complications are often treated with therapeutic drugs, creating a market for ocular drug delivery technologies worth over 10 billion dollars. However, current delivery options are often ineffective, require high dosage frequencies and concentrations, and lead to poor patient compliance. To better realize the sustained bioavailability of ocular drugs, recent research has turned to novel ocular drug delivery systems to achieve desired characteristics that include prolonging drug residence time at the site of administration, increasing drug permeation across ocular barriers, controlling release, and localizing drug exposure to targeted tissues.

While drug application to the surface of the cornea is a very popular approach, the inherent anatomical and physiological characteristics of the ocular surface act as a barrier to protect the eye against the penetration of foreign substances. As a result, the bioavailability of topical medications in the anterior chamber is typically less than 5% and 0.5% for lipophilic and hydrophilic drugs, respectively. Intravitreal injection to the posterior segment of the eye is able to increase bioavailability in the vitreous by avoiding corneoscleral barriers. However, frequent injections run the risk of causing a retinal detachment or hemorrhage, among other complications.

U.S. Pat. No. 9,192,511 discusses biodegradable ocular implants and delivery systems intended for vitreous implantation entirely within the eye.

U.S. Pat. No. 6,217,895 discusses a sustained corticosteroid release device implanted within the posterior segment of the eye.

U.S. Pat. No. 8,529,492 discusses a method for treating an ocular condition which involves implanting a drug delivery device within the suprachoroidal space.

U.S. Pat. No. 9,012,437 discusses a method for treating an inflammation-mediated condition by implanting a bioerodible device into the vitreous of the eye.

While the above patents demonstrate a number of ocular implants intended to treat conditions in the eye, their intended implant location is either in the vitreous or the suprachoroidal space. These devices are inherently difficult to remove if any complications arise, and do not offer the clinician an opportunity to examine the device following implantation. It would be safer to provide an ocular drug delivery system which is easily explanted, and easily viewed through the cornea.

U.S. Pat. No. 5,378,475 discusses a double polymer coated inner core with selective permeability to an agent contained within the inner core wherein said agent is intended to cause local or systemic physiological or pharmacological effects on a mammalian organism.

U.S. Pat. No. 8,574,659 discusses a sustained drug delivery system comprising a tube filled with a drug core.

U.S. Pat. No. 7,708,711 discusses a method for treating an ocular disorder by placing an implant which contains a therapeutic wherein the implant drains aqueous humor from the anterior chamber into a physiologic outflow pathway.

SUMMARY

In an effort to avoid the inefficiencies and risks associated with current ocular drug administration techniques, methods for developing implantable ocular drug delivery devices have been pursued. These technologies are designed to achieve prolonged release of the therapeutic inside the eye in a controlled manner. In at least some cases, implantable ocular delivery systems are more efficient at obtaining their intended therapeutic benefits, decrease the risk of unintended systemic delivery, and lead to better patient compliance. In some embodiments, the devices disclosed herein drain or shunt aqueous humor to the tear film, avoiding the traditional physiologic outflow pathways in order to provide adequate pressure reduction such that blindness is mitigated or prevented.

In one aspect, this disclosure is directed to an implantable ocular drug delivery device. Such an implantable ocular drug delivery device may include a body that has a distal end portion and a proximal end portion. The body has a longitudinal length sufficient to position the distal end portion in an anterior chamber of an eye and the proximal end portion in a tear film of the eye when the body is implanted in a sclera of the eye. The body can define an internal chamber and an inlet to the internal chamber through an outer surface of the body. Accordingly, the internal chamber is communicative to an exterior region around the body via the inlet. The implantable ocular drug delivery device can also include a pharmacological agent within the internal chamber.

Such an implantable ocular drug delivery device may optionally include one or more of the following features. The body may define a lumen extending between the distal end portion and the proximal end portion. Such a lumen may establish fluid communication between the anterior chamber and the tear film when the body is implanted in the sclera of the eye. In some embodiments, material of the body separates an entirety of the internal chamber from the lumen. The body may define one or more fenestrations configured to allow for tissue ingrowth. In some embodiments, an inlet portion of the internal chamber has a smaller cross-sectional area than a remaining portion of the internal chamber that is located farther internally than the inlet portion. Alternatively, in some embodiments an inlet portion of the internal chamber has a larger cross-sectional area than a remaining portion of the internal chamber that is located farther internally than the inlet portion. The body may define one or more additional inlets to the internal chamber (i.e., multiple inlets to a single internal chamber may exist). In some embodiments, the body defines one or more additional internal chambers and corresponding inlets to the one or more additional internal chambers. That is, the body may define two or more internal chambers with respective separate inlets. In some embodiments, each of the two or more internal chambers have the same shape. Alternatively, in some embodiments the two or more internal chambers may have differing shapes.

The pharmacological agent may be a first pharmacological agent, and the device may include a second pharmacological agent in the one or more additional internal chambers. In some embodiments, the first and second pharmacological agents are different types of pharmacological agents. Alternatively, in some embodiments, each of the two or more internal chambers can contain the same type of pharmacological agent. The proximal end portion is laterally wider than the distal end portion in some embodiments.

In another aspect, this disclosure describes methods of using the implantable ocular drug delivery devices described herein to treat mammalian patients. Such methods include the release, from the implantable ocular drug delivery devices described herein, of one or more pharmacological agents to aqueous humor within an anterior chamber of an eye of the patients.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

BRIEF DESCRIPTION OF THE DRAWINGS

FIG. 1a is a top view of an example implantable ocular drug delivery device utilizing two tapered drug-releasing entities (DREs) disposed between an outer polymer housing and within an inner biocompatible polymer layer. The drug delivery device includes a microchannel to conduct fluid from the anterior chamber to the tear film and fenestrations to anchor the device to tissue.

FIG. 1b is a side view of the ocular drug delivery device of FIG. 1a.

FIG. 2a is a top view of another example implantable ocular drug delivery device utilizing two multi-zone DREs with discrete release profiles disposed between an outer polymer housing and within an inner biocompatible polymer layer. The drug delivery device includes a microchannel to conduct fluid from the anterior chamber to the tear film and fenestrations to anchor the device to tissue.

FIG. 2b is a side view of the ocular drug delivery device of FIG. 2a.

FIG. 3a is a top view of another example implantable ocular drug delivery system utilizing two constant-width DREs disposed between an outer polymer housing and within an inner biocompatible polymer layer. The drug delivery device includes a microchannel to conduct fluid from the anterior chamber to the tear film and barbs on the outer surface to anchor the device to tissue.

FIG. 3b is a side view of the ocular drug delivery device of FIG. 3a.

FIG. 4a is a top view of another example implantable ocular drug delivery device utilizing two DREs disposed between an outer polymer housing and within an inner biocompatible polymer layer. The DREs maintain fluid contact with the aqueous humor through several laser-cut fenestrations in the rounded tail end. The drug delivery device includes a microchannel to conduct fluid from the anterior chamber to the tear film and barbs on the outer surface to anchor the device to tissue.

FIG. 4b is a side view of the ocular drug delivery device of FIG. 4a.

FIG. 5b is a side view of the ocular drug delivery device of FIG. 5a.

FIG. 6a is a top view of another example implantable ocular drug delivery device utilizing three staged and discrete DREs disposed between an outer polymer housing and within an inner biocompatible polymer layer. The drug delivery device includes a microchannel to conduct fluid from the anterior chamber to the tear film and barbs on the outer surface to anchor the device to tissue.

FIG. 6b is a side view of the ocular drug delivery device of FIG. 6a.

FIG. 7a is a top view of another example implantable ocular drug delivery device utilizing a single DRE disposed between an outer polymer housing and within an inner biocompatible polymer layer. The device contains barbs on the outer surface as well as fenestrations to anchor the device to tissue.

FIG. 7b is a side view of the ocular drug delivery device of FIG. 7a.

Like reference numbers represent corresponding parts throughout.

DETAILED DESCRIPTION OF EXAMPLE EMBODIMENTS

Figure 5A:
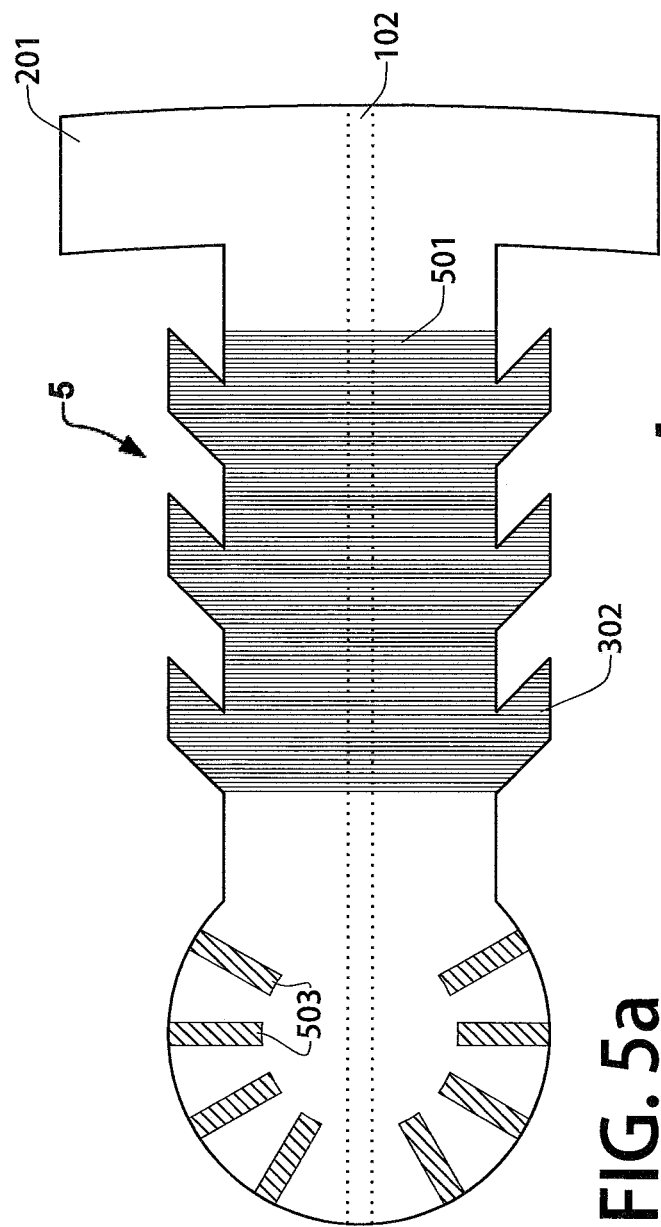
FIG. 5a is a top view of another example implantable ocular drug delivery device utilizing eight discrete DREs disposed between an outer polymer housing and within an inner biocompatible polymer layer. The drug delivery device includes a microchannel to conduct fluid from the anterior chamber to the tear film and barbs on the outer surface to anchor the device to tissue.

FIG. 1a is a top view of a first example embodiment trans-scleral implant (or simply "device 1") in which at least a portion of the implant is present within the anterior chamber when the device 1 is implanted in an eye. This example embodiment may act both as an aqueous shunt and as a non-biodegradable intraocular drug delivery implant. FIG. 1b depicts a side view of device 1. An inner polymer layer 106 is disposed between the top and bottom outer polymer layers 105. The outer polymer layers 105 may be composed of thermoplastic polyurethane or a similar biocompatible polymer. In this embodiment, a microchannel 102 is disposed within the inner polymer layer 106 and runs through the length of the device to shunt aqueous humor from the anterior chamber of the eye to the tear film, lowering the intraocular pressure of the patient. In some embodiments, the inner polymer layer 106 and channel walls 107 are composed of a hydrophilic, anti-biofouling polymer to prevent the formation of biofilm over the lifetime of the implant.

Device 1 is intended to be implanted from the conjunctiva 802 to the anterior chamber 805 through scleral tissue 801

Figure 8:
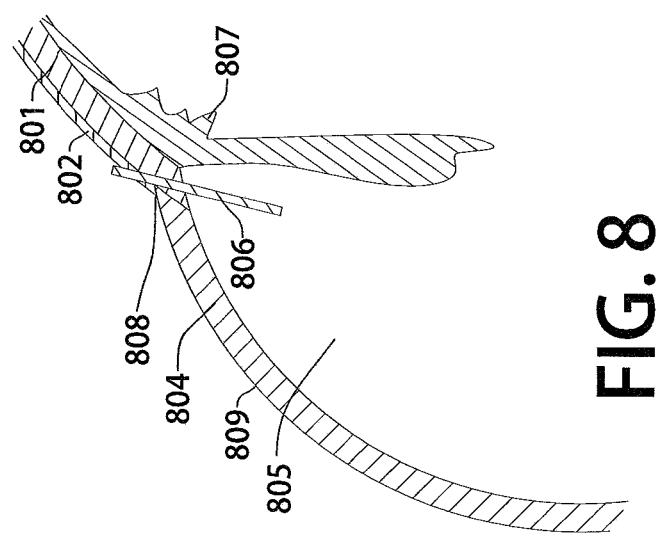
FIG. 8 is an anatomical depiction of an eye, demonstrating placement of an example device through the sclera located partially within the anterior chamber.
Figure 9:
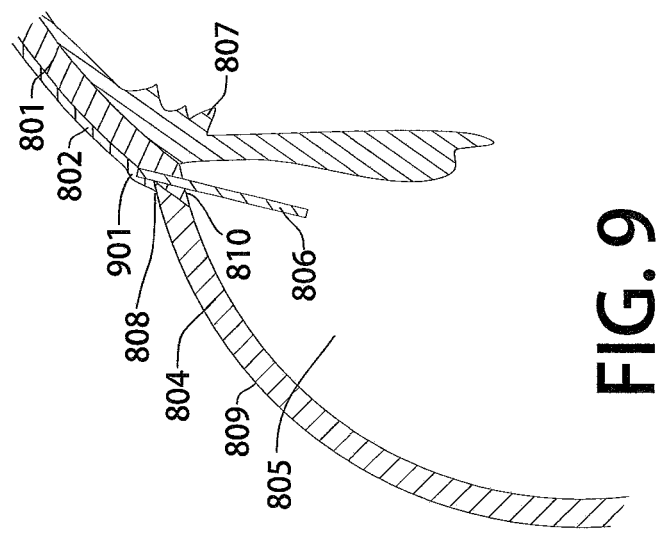
FIG. 9 is an anatomical depiction of an eye, demonstrating placement of an example device through the sclera with a layer of conjunctiva tissue placed over the crossbar tab of the device.

(e.g., as depicted in FIGS. 8 and/or 9). A stab-incision is made within several millimeters of the limbus 901 through scleral tissue 801 using a keratome blade about 0.1 mm larger than the width of the body of device 1. In some embodiments, the stab incision is made within about 2 mm of the limbus in conjunctival tissue 802. In preferred embodiments, the stab incision is made within 1 mm of the limbus within conjunctival tissue 802. The keratome blade size should be smaller than the largest width of the device 1 at the crossbar tab 101. The crossbar tab 101 is intended to abut the outer surface of the eye as shown in FIG. 8. Alternatively, the crossbar tab 101 may be covered by a layer of conjunctiva placed over the crossbar tab 101 as shown in FIG. 9, in which case the crossbar tab 101 abuts the scleral tissue 801. Device 1 also contains at least two elongated fenestrations 103 through which scleral tissue is intended to grow and anchor the device. While device 1 depicts the crossbar tab 101 as having rounded corners 111, it may be beneficial for the corners of the crossbar tab 101 to be sharp (e.g., as shown in FIG. 2-7) since rounded corners 111 on the surface of the eye may predispose the implant to conjunctival overgrowth. In some embodiments (such as those without a microchannel 102), the rounded corners 111 are intentionally included to encourage conjunctival overgrowth.

Proper placement of the device is important as an incision through corneal tissue 804 may lead to future endothelial cell loss. Conversely, incisions made distant from the limbus in conjunctival tissue 802 are more prone to conjunctival overgrowth and may prevent the rounded distal tip of the device 1 from entering the anterior chamber.

Flanking the channel 102 of device 1 and also disposed within the inner polymer layer 106 are two drug-releasing entities (DREs) 104 enclosed by the same polymer that comprises the inner polymer layer 106 and channel walls 107. In this embodiment, each DRE 104 comprises a reservoir that stems from a narrow inlet 109. Each DRE 104 is in direct contact with aqueous humor via the narrow inlet 109. Other than the channel 102 and the two DRE inlets 109, the remainder of the implant is impermeable to aqueous fluids.

Drug releasing entities (DREs) can be biodegradable, non-biodegradable, solid, or semi-solid in form. Biodegradable DREs may be constructed from a homogenous polymeric matrix in which a therapeutic is embedded within the pores of a biodegradable polymer matrix that is physically and/or chemically cross-linked; the DREs may have multiple strata composed of heterogeneous polymeric biodegradable matrices and potentially different therapeutics or therapeutic concentrations within each stratum; the DREs may contain a therapeutic present within or conjugated to a micro- or nanoparticle that is embedded within one or more polymeric matrices that degrade over time. In some embodiments, the degradation products of the biodegradable matrices are biocompatible with the surrounding tissue. The DREs can also comprise a combination of these configurations.

Non-biodegradable DREs may be constructed from a homogenous polymeric matrix in which a therapeutic is embedded within the pores of a non-biodegradable polymer matrix that is physically and/or chemically cross-linked; the DREs may have multiple strata composed of heterogeneous polymeric non-biodegradable matrices and potentially different therapeutics or therapeutic concentrations within each stratum; the DREs may contain a therapeutic present within or conjugated to a micro- or nanoparticle that is embedded within one or more polymeric matrices. The DREs can also comprise a combination of these configurations. Non-biodegradable matrices release medications after swelling of their pores occurs following the influx of aqueous humor through the inlets 109.

Any substance, molecule, or therapeutic intended to mitigate direct or subsidiary effects of a disease or complication may be incorporated in a DRE. Additionally, any substance, molecule, or therapeutic designated to stimulate or support a desired process or effect may be employed in a DRE. Additionally, the therapeutic can exist in a solid or semi-solid state within the DREs, without the presence of a polymeric matrix. The DREs can also comprise a combination of these outlines.

Therapeutics may include accepted pharmaceutical agents, naturally occurring macromolecules and their polymers (e.g., nucleic acid vectors for uptake into cells and subsequent protein expression), synthetic proteins, and the like. The released therapeutic and its excipient or carrier can be designed for localized delivery to an intraocular structure or for systemic delivery outside the eye. In either circumstance, it may be intended for the treatment of an ocular disease or for a complication outside the eye.

Example therapeutics may include but are not limited to: steroidal anti-inflammatory drugs: such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, 6-mannose phosphate, hydrocortisone acetate, dexamethasone 21-phosphate, prednisolone 21-phosphate, fluoromethalone, triminolone, or prednisolone acetate; antimetabolites such as folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), and pyrimidine analogs (e.g., ancitabine, azacitidine, 6-azauridine, carmofur, cytarabine, doxifluridine, emitefur, enocitabine, floxuridine, fluorouracil, gemcitabine, tegafur); antibacterial antibiotics such as aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, florfenicol, thiamphenicol), ansamycins (e.g., rifamide, rifampin, rifamycin sv, rifapentine, rifaximin), β-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, cefpiramide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefmetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin), chloramphenicol, gentamycin, nitrofurazone; synthetic antibacterials such as 2,4-Diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, n2-formylsulfisomidine, n4-β-d-glucosylsulfanilamide, mafenide, 4'-(methylsulfamoyl) sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, n4-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibornol); antifungal antibiotics such as polyenes (e.g., amphotericin b, candicidin, dermostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin); synthetic antifungals such as Allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate); antineoplastics such as antibiotics and analogs (e.g., aclacinomycins, actinomycin f1, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g. folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur); glaucoma therapeutics such as: beta-blockers (e.g. timolol, betaxolol, atenolol, prostaglandins (e.g., metabolite derivatives of arachindonic acid), lipid-receptor agonists or prostaglandin analogues (e.g. bimatoprost, travoprost, latanoprost, unoprostone etc), alpha-adrenergic agonists, brimonidine or dipivefrine, carbonic anhydrase inhibitors (e.g. acetazolamide, methazolamide, dichlorphenamide, diamox, ethoxzolamide), and neuroprotectants (e.g. nimodipine and related compounds), apraclonidine; anti-viral agents such as: Trifluorothymidine, acyclovir, ganciclovir, DDI, AZT, foscamet, vidarabine, trifluorouridine, idoxuridine, ribavirin, protease inhibitors and anti-cytomegalovirus agents, antiallergenics (e.g. methapyriline; chlorpheniramine, pyrilamine, prophenpyridamine, trisodium phosphomonoformate), nonsteroidal anti-imflammatory agents such as: Cyclooxygenase-1 (COX-1) inhibitors (e.g., acetylsalicylic acid (e.g. ASPIRIN from Bayer AG, Leverkusen, Germany), ibuprofen (e.g. ADVIL from Wyeth, Collegeville, Pa., indomethacin, mefenamic acid), COX-2 inhibitors (e.g. CELEBREX from Pharmacia Corp., Peapack, N.J.) COX-1 inhibitors, (e.g. NEPAFENAC), nonsteroidal glucocorticoid antagonists; immunosuppressive agents such as: Sirolimus (RAPAMUNE, from Wyeth, Collegeville, Pa.), or matrix metalloproteinase (MMP) inhibitors (e.g., tetracycline and tetracycline derivatives); anticlotting agents such as: heparin, antifibrinogen, fibrinolysin, tissue plasminogen activator (tPA), and the like; antidiabetic agents such as: acetohexamide, chlorpropamide, glipizide, glyburide, tolazamide, tolbutamide, insulin, aldose reductase inhibitors; anticancer agents such as: 5-fluorouracil, adriamycin, asparaginase, azacitidine, azathioprine, bleomycin, busulfan, carboplatin, carmustine, chlorambucil, cisplatin, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, fluoxymesterone, flutamide, goserelin, hydroxyurea, ifosfamide, leuprolide, levamisole, lomustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine; antiallergenic agents such as: antazoline, methapyriline, chlorpheniramine, pyrilamine and prophenpyridamine; immunomodulators such as: tumor necrosis factor inhibitors (e.g. thalidomide); and other potential therapeutic agents such as: ace-inhibitors, endogenous cytokines, cytokines, agents that influence basement membrane, adrenergic agonists or blockers, cholinergic agonists or blockers, aldose reductase inhibitors, analgesics, anesthetics, antiallergics, antivirals, antiprotozoals, anti-infective agents, antitumor agents, antiangiogenic agents (e.g. anti-VEGF agents), small molecule drugs, proteins, nucleic acids, polysaccharides, biologics, lipids, hormones, steroids, glycolipids, glycoproteins, and other macromolecules. Examples include: endocrine hormones such as pituitary, insulin, insulin-related growth factor, thyroid, growth hormones; heat shock proteins; immunological response modifiers such as muramyl dipeptide, cyclosporins, interferons (including α, β, and γ interferons), interleukin-2, cytokines, FK506 (an epoxy-pyrido-oxaazcyclotricosine-tetrone, also known as Tacrolimus), tumor necrosis factor, pentostatin, thymopentin, transforming factor beta2, erythropoetin; antineogenesis proteins (e.g., anti-VEGF, Interferons), brain nerve growth factor (BNGF), ciliary nerve growth factor (CNGF), vascular endothelial growth factor (VEGF), and monoclonal antibodies directed against such growth factors, vaccines, therapeutics that inhibit cell growth or promote cell death, that can be activated to inhibit cell growth or promote cell death, growth factors, proteins, peptides or peptidomimetics, bioactive agents, photosensitizing agents, radionuclides, toxins, signaling modulators, anti-cancer antibiotics, anti-cancer antibodies, angiogenesis inhibitors, radiation therapy, chemotherapeutic compounds, intraocular pressure reducing agent, cell transport/mobility impending agents such as colchicine, vincristine, cytochalasin B and related compounds, decongestants (e.g. phenylephrine, naphazoline, and tetrahydrazoline), miotics, muscarinics, anticholinesterases (e.g. pilocarpine, carbachol, di-isopropyl fluorophosphate, phospholine iodine, demecarium bromide), mydriatics (e.g. atropine sulfate, cyclopentolate, homatropine, scopolamine, tropicamide, eucatropine), sympathomimetics (e.g. epinephrine, vasoconstrictors, vasodilators), pain killing agents (e.g. lidocaine and related compounds, benzodiazepam and related compounds).

Any pharmaceutically acceptable form of such a compound may be employed (e.g. the free base or a pharmaceutically acceptable salt or ester thereof). Pharmaceutically acceptable salts, for instance, include sulfate, lactate, acetate, stearate, hydrochloride, tartrate, maleate, and the like.

In addition to active therapeutics, the DREs may contain release enhancers (e.g. swelling agents), release-hindering agents (e.g. solubility diminishing agents), buffering agents, prodrugs, drug preservatives, diluents, drug carriers (e.g. membrane permeation enhancers), surfactants, and other excipients of the like to make the therapeutic more compatible, stable, soluble (or insoluble), release at a preferred rate, or reach a desired anatomical destination.

In the example embodiment of device 1, an influx of aqueous liquid diffuses across the two inlets 109 and enters the DREs 104. The aqueous fluid then interacts with and alters the physical character of the DREs 104 by way of swelling, degradation, dissolution, etc. This remodeling gives rise to a diffusion-based efflux of a therapeutic out of the DREs 104 and into the aqueous environment where it can then be transported to its targeted anatomical location. This process occurs at a preferential rate, for a desired period of time. After the implant has resided in the anterior chamber for a sufficient length of time, it can be explanted and replaced with a fully stocked implant.

The amount of therapeutic released is relatively small during the time in which aqueous fluid diffuses through the narrow inlet 109 but has not yet reached the larger portion of the reservoir 110. Once the aqueous fluid reaches the larger portion of the reservoir 110, a more significant burst release may occur. This may be followed by a period of constant (near-zero-order) release before the remainder of the therapeutic effluxes from the implant at a tapered rate. The duration of these three pharmacokinetic phases will depend on the number, shape, and size of the inlets contained within the implant, along with the geometry of the cavities defining the DREs. If larger release half-lives of the therapeutic are desired, for example, the combined surface area of the inlets may be reduced.

The geometric design and dimensions of the implantable devices described herein and the DREs described herein can consequently be altered to accommodate a variety of therapeutics as well as a variety of human and nonhuman ocular anatomies. Additionally, multi-zone or staged release patterns can be accomplished, as in device 2 (FIGS. 2a and 2b), by providing varied geometry with respect to the inlet opening 202. The device footprint can be reduced to allow better biointegration in smaller species, such as canine, feline, leporine, and the like. Similarly, the footprint can be increased to allow better biointegration in larger species such as equine, bovine, ursine, and the like. The devices depicted in the example embodiments described herein are suitable for human or canine anatomy, with an overall length between about 1 mm and 10 mm, a width between about 0.2 mm and 3 mm, and a height between about 0.05 mm and 1 mm. Preferred embodiments have an overall length between about 2 mm and 4 mm, a width between about 0.5 mm and 2 mm, and a height between around 0.1 mm and 0.5 mm.

The example embodiment depicted in FIG. 2a and FIG. 2b (or simply "device 2") is identical to device 1 except for its pharmacokinetics and crossbar tab 201 shape. The geometry of the DREs in this embodiment contain two distinct regions defined by the width and profile of the narrow inlet portion 202. The amount of time necessary for the aqueous humor to diffuse through the narrow inlet portion 202 is prolonged compared to device 1, leading to two different pharmacokinetic release patterns as a function of the length of implantation. An initial burst release and subsequent zero-order release kinetic is obtained initially, however, once the aqueous humor reaches the larger portion of the reservoir 203, a more significant burst release may occur followed by a second period of constant (near-zero-order) release before the remainder of the therapeutic effluxes from the implant at a tapered rate. Similar to device 1, device 2 contains a microchannel 102 disposed between the outer polymer layers 105 which serves to conduct fluid from the anterior chamber 805 to the tear film 809 (FIGS. 8 and 9). In this way, device 2 may act both as a drug-delivery device and an intraocular pressure reducing shunt. Device 2 also contains fenestrations 103 that are intended to anchor the device within scleral tissue 801 after implantation.

The example embodiment depicted in FIG. 3a and FIG. 3b (or simply "device 3") contains two DREs 301 disposed between the outer polymer layers 105 and within the inner polymer layer 106. The DREs 301 depicted in device 3 maintain a constant width along the length of the device 3. This embodiment differs from device 1 and 2 in that the pharmacokinetic release pattern is intended to be a constant rate (near zero-order) for the lifetime of the implant. In this design, a significant burst release will occur near the time of implantation. This may be followed by a period of constant rate (near-zero-order) release before the remainder of the therapeutic effluxes from the implant at a tapered rate. The outer edges of device 3 contain barbs 302 that provide increased tissue-contacting surface area to be anchored by the surrounding scleral tissue 801. The barbs 302 also prevent migration and dislodgment of the device 3 once implanted. Device 3 maintains sharp corners on the crossbar tab 201 that is intended to limit conjunctival overgrowth.

In some embodiments containing a microchannel 102, the microchannel 102 is intended to treat and prevent elevated intraocular pressure. The microchannel 102 width, height, and length are tailored to provide adequate fluidic resistance to prevent hypotony, but also enough facility to prevent the progression of blindness associated with elevated intraocular pressures. Ideally, the microchannel 102 provides an adequate hydraulic resistance such that the patient's intraocular pressure normalizes between eight and twelve mmHg after implantation and patient ceasing administration of ocular drugs, for example, travoprost, latanoprost, or the like.

In some embodiments containing a microchannel 102, the microchannel 102 is intended to treat and prevent ocular diseases characterized by a lack of lacrimal tear production such as dry eye. The microchannel 102 width and height are tailored to provide adequate resistance to prevent hypotony, but also enough facility to bathe the eye in aqueous humor.

In some embodiments, at least a portion of the external surface of the outer polymer layer 105 may be textured, such as by stippling, cross-hatching, waffling, roughening, and the like. In some embodiments, this can be accomplished by laser engraving with very low laser energy. In some embodiments, this can be accomplished by chemical means through spatially defined plasma treatments as in FIG. 5a and FIG. 5b (referring to external surface portion 501). In such an embodiment, a protection layer may be aligned with the device such that a small window is situated over areas intended for texturing. Exposing the device and protection layer to plasma (oxygen plasma, air plasma, nitrogen plasma, and the like) will increase the surface roughness of the exposed portion(s) of the device and potentially alter the exposed surface chemical group. In this way, spatially defined areas of the device may be nano-textured 501 and/or chemically altered to increase the ability of mammalian cells to adhere.

In some embodiments, the outer polymer layer 105 of the devices described herein can be formed of a material such as polyethylene terephthalate ("PET"), Poly(methyl methacrylate) ("PMMA"), Polyurethane ("PU"), Polycarbonate ("PC"), Polyvinyl chloride ("PVC"), Polyvinyl alcohol ("PVA"), Polystyrene ("PS"), Thermoplastic polyurethane ("TPU"), Polyethylene ("PE"), Polysulfone, Polyethersulfone ("PES"), Sulfonated Polyethersulfone ("SPES"), Polybutylene terephthalate ("PBT"), Polyhydroxyalkanoates ("PHAs"), Silicone, Parylene, Polypropylene ("PP"), Fluoropolymers, Polyhydroxylethylmethacrylate ("pHEMA"), Polyetherketoneketone ("PEKK"), Polyether ether ketone ("PEEK"), Polyaryletherketone ("PAEK"), Poly(lactic-co-glycolic acid) ("PLGA"), Polytetrafluoroethylene ("PTFE"), Polyvinylidene fluoride ("PVDF"), or Polyacrylic acid ("PAA"). In some embodiments, the outer polymer layer 105 may be composed of a combination of two or more materials.

The example embodiment depicted in FIG. 4a and FIG. 4b (or simply "device 4") in which at least a portion of the implant device 4 is positionable within the anterior chamber 805 (FIGS. 8 and 9) may double as an aqueous shunt and as an intraocular drug delivery system. A microchannel 102 runs through the length of the device 4 to shunt aqueous humor from the anterior chamber 805 of the eye to the tear film 809, lowering the intraocular pressure of the patient. In some embodiments, the channel walls 107 are composed of a hydrophilic, anti-biofouling polymer.

Flanking the channel 102 are two biocompatible DREs 401 that can be enclosed by the same polymer that comprises the channel walls 107. In this embodiment, each DRE 401 is comprised of a reservoir that is exposed to the aqueous environment by way of multiple inlets 402 on both the top 403 and bottom 404 surfaces of the implant device 4. These inlets 402 are preferably circular with a diameter between about 1 micron and 100 microns or larger, but can be any geometric shape so long as the size is smaller than the width of the DRE 401. When the device 4 is implanted in an eye, the inlets 402 will reside within the anterior chamber 805, below the ocular tissue line 810 (FIGS. 8 and 9). The inlets 402 may be left open and exposed to the environment after manufacturing, or temporarily sealed until just before or during implantation. The size of the inlets 402 can be controlled after the DREs 401 have been fabricated using singulation methods known in the art such as laser processing, die-cutting, and the like. In this way, the pharmacokinetics can be altered and controlled in the final assembly step without adjusting the size of the DREs 401 during manufacturing.

These inlets 402 may also act as semipermeable membranes. In at least one embodiment, the inlets 402 are covered with a selectively permeable membrane to aqueous humor, composed of for example ethylene-vinyl acetate (EVA). In at least one embodiment, the inlets 402 are covered with a selectively permeable membrane to a therapeutic and its excipients, composed of for example polyvinyl alcohol. Other than the channel 102 and the inlets 402, the remainder of the implant device 4 is impermeable to aqueous fluids.

Figure 5B:
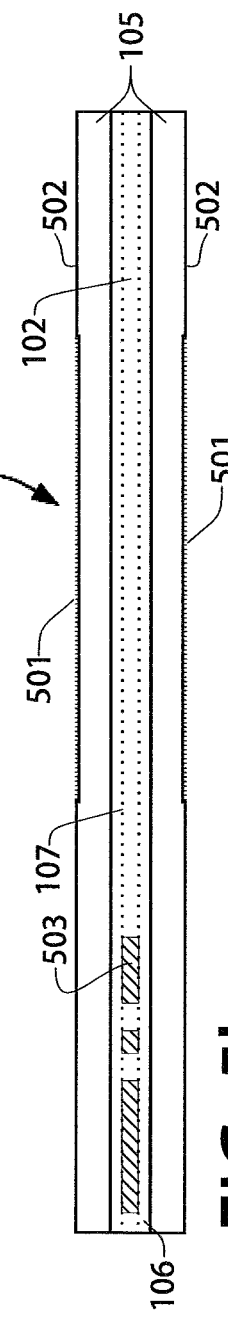

The example embodiment depicted in FIG. 5a and FIG. 5b (or simply "device 5") contains eight separated DREs 503, one hydrophilic microchannel 102 that runs the length of the device 5, and two plasma treated surface portions 501. In this embodiment, plasma treatment at the surface portions 501 is used to encourage better bio-integration and more consistent cellular anchoring which leads to improved healing, reduced dislodgement and migration, and a faster recovery for patients following implantation. Barbs 302 are included on the sides of device 5 to further improve cellular anchoring and prevent dislodgement. Device 5 contains eight unique DREs 503 which can each contain a separate, different therapeutic (or two or more DREs 503 can contain a same therapeutic). Device 5 demonstrates the ability to provide a large number of therapeutics in the same implant.

Generally speaking, in vitro devices that come into contact with protein-rich solutions, such as those present in mammalian anterior chambers of the eye, are subject to nonspecific protein adsorption that can either partially or entirely compromise the functionality of the microchannel. In at least some of the implantable device embodiments described herein, the microchannel 102 is able to resist bacterial, cellular, and protein adsorption by way of careful material selection.

In some embodiments, the inner polymer layer 106 composing the channel walls 107 and defining the geometric area of the DRE may be composed of a material such as polyethylene glycol ("PEG") (e.g., an acrylate-PEG-acrylate such as triethylene glycol dimethacrylate), a polymerized zwitterion, N-(2-methacryloyloxy)ethyl-N, N-dimethylammonio propanesulfonate ("SPE"), N-(3-methacryloylimino) propyl-N, N-dimethylammonio propanesulfonate ("SPP"), 2-(methacryloyloxy)ethylphosphatidylcholine ("MPC"), 3-(2'-vinyl-pyridinio)propanesulfonate ("SPV")), Poly(2-oxazoline)s (e.g. Poly(2-ethyl-2-oxazoline)), Poly(hydroxyfunctional acrylates) (e.g. Poly(2-hydroxyethyl methacrylate); Poly(glycerol)), poly(vinylpyrrolidone), peptides or peptoids (e.g. Poly(amino acid) or Poly(peptoid)). In some embodiments, the inner polymer layer 106 may be composed of a combination of materials.

The example embodiment depicted in FIG. 6a and FIG. 6b (or simply "device 6") does not contain a microchannel (e.g., like the microchannel 102 of some other devices described herein), and accordingly serves only as a drug delivery system. Three unique DREs 601, 602, 603 are located at the tail end of the device 6 comprised of various biodegradable matrices. In this embodiment, the outer most DRE matrix 601 comprises a biodegradable matrix which encapsulates tissue plasminogen activator (TPA), which has been shown to reduce the concentration of fibrin in the anterior chamber 805 (FIGS. 8 and 9) following implantation. The inner most DREs 602 603 contain therapeutics intended to treat glaucoma such as latanoprost. The device 6 contains two barbs 302 extending laterally from each side of a mid-body portion of the outer surface, which help to anchor the device 6 within the scleral tissue 801.

In at least one embodiment, the inner surfaces 604 of the outer polymer layers 105 are chemically altered to increase the bonding strength between the inner polymer layer 106 and the outer polymer layers 105. This can be accomplished by attaching chemical moieties to the inner surfaces 604 of the outer polymer layers 105. Plasma treatment is regularly used in the art to alter chemical groups on the surface of certain materials. For instance, oxygen plasma treatment can be used to increase the density of hydroxyl groups on the surface of polymers. After plasma treatment, the newly formed hydroxyl groups provide good linkage sites for chemical moieties such as silane coupling agents. If the inner polymer layer 106 is polymerized using an acrylate-based approach, such as with polyethylene glycol diacrylate, the silane coupling agent may contain an active silane group on one end of the coupling agent, and an acrylate group on the opposing end of the coupling agent. In this way, the inner surfaces 604 of the outer polymer layers 105 may be covalently bonded, thus creating a stronger bond between inner polymer layer 106 and the outer polymer layers 105.

The example embodiment depicted in FIG. 7a and FIG. 7b (or simply "device 7") does not contain a microchannel (e.g., like the microchannel 102 of some other devices described herein), and can accordingly serve as a drug delivery system only. This example embodiment contains a single DRE 701 that extends along most of the length of the device 7 (e.g., about 70% to about 90%, or about 50% to about 90%, of the length of the device 7). In some embodiments, the DRE 701 possesses an inlet that is radially configured at its distal end and extends proximally until it meets the inner polymer layer 106. That is, the inlet of device 7 can span the entire outer edge of the body at the distal end portion of the device 7 (e.g., in a "U shape"). The device contains four barbs 302 extending transversely from each side of the device 7, with a fenestration 103 placed immediately interior to the four barbs 302. The barbs 302 and fenestrations 103 are both intended to increase the cellular anchoring and prevent micromotion, migration, and dislodgement of the implant device 7.

In this embodiment, the DRE 701 decreases in width as it traverses the length of the device 7. That is, the DRE 701 is widest near the distal end portion of the device 7, and becomes narrower as the DRE extends toward the proximal end of the device 7. The consequent pharmacokinetic release curve will demonstrate a decreasing therapeutic concentration release rate as time passes. This may be beneficial for a number of reasons such as a defined tapering schedule of ocular drugs. In one such circumstance, a patient may be instructed to slowly reduce the application of a certain eye drop over time, from five drops a day to two drops a day, and the shape of this DRE 701 may suffice to accomplish the same goal.

In certain cases, it may be valuable to release therapeutics directly to the ocular tissue instead of the anterior chamber 805. In at least some embodiments, one or more DREs possess inlets that abut and directly communicate with the ocular tissue surrounding the barbs 302. In this way, interstitial fluid from the scleral tissue that surrounds the barbs may interact with the DRE to provide drug release over time. In one such embodiment, a DRE may contain an anti-inflammatory therapeutic to reduce inflammation following implantation.

Drug Releasing Entities (Additional Information)

In at least some embodiments of the devices described herein, the following considerations may be altered to control the pharmacokinetics and dosage capacity of the drug delivery system: the number of DREs, the geometry of DREs, such as height or volume, the number of inlets, the geometry of inlets, and the location of inlets, the nature of the polymers incorporated in the DREs (e.g., permeability), and the characteristics of the therapeutics and their respective excipients (e.g., solubility). These considerations may also be dependent on the conditions to be treated, the patient receiving the implant, and the desired period of therapeutic administration. In some embodiments, a biodegradable DRE can be described by at least one of three forms: 1) A homogeneous biodegradable polymeric matrix, 2) At least two heterogeneous biodegradable polymeric matrices, 3) A collection of micro- or nanoparticles embedded in at least one polymeric matrix in which at least one therapeutic is contained therein by way of encapsulation or conjugation.

Each of these biodegradable forms will possess three phases of drug delivery following implantation: 1) A period of burst release, 2) A period of near zero-order release, and 3) a time of tapered release where a minimal amount of at least one therapeutic is delivered from the DRE to the anterior chamber of the eye. The duration of these three periods will depend on the DRE cavity geometry and the open surface area of the inlets, the nature of the biodegradable DRE form utilized in that embodiment, such as the kind of polymer used for the matrix, the polymeric crosslinking density, the type of micro- or nanoparticle used, and the nature of the therapeutics incorporated. The amount of therapeutic delivered and/or the rate of release during each stage will also depend on the biodegradable DRE form in addition to the concentration of the therapeutic present within the DRE.

In a homogeneous biodegradable polymeric matrix, the therapeutic is embedded within the pores of a biodegradable polymer matrix. The polymeric matrix is composed of one monomer or polymer, which can be natural or synthetic. These monomers can be constructed into a matrix (or solidified) by way of chemical and/or physical crosslinking. In the former, monomers are covalently bonded to each other, customarily after a stimulus is applied, such as exposure to UV light, heating, or the like. In the latter, polymers are bonded together through noncovalent means such as through ionic bonding, electrostatic attraction, and the like. The polymers used in the DRE can be created via a number of polymerization processes. These include but are not limited to chain-reaction polymerization, such as free radical polymerization, and condensation polymerization. The pore size of the homogeneous matrix will be contingent on the characteristics of the polymer that affect the crosslinking density, such as the length of its chains. Crosslinking densities will affect the rate of release and are preferably constant but may differ across the matrix.

Therapeutics can be combined with a matrix by mixing a biodegradable polymer or constituents of a polymer (monomer units and a possible initiator) in solution with at least one therapeutic in solution, then gelling or solidifying the mixture via application of at least one external stimulus. Alternatively, a solid form of the therapeutic can be incorporated into the pores of the aforementioned polymeric matrix. The concentration distribution of the therapeutic within a matrix is preferably monolithic, or constant. However, the concentration can possess a gradient across a matrix for the sake of achieving a preferred pharmacokinetic curve.

The resulting gel or solid may be shaped into a preferred geometry through methods such as embossing, micro-molding techniques, such as injection molding and the like, lithography techniques, such as photolithography and the like, extrusion, co-extrusion, imprinting, or heat compression. The shaped gel or solid can then be placed into a DRE cavity in the interior of the device. Alternatively, the therapeutic/polymer mixture can be delivered into the cavity in the interior of the implant in solution form and the polymer subsequently cross-linked, polymerized, or solidified.

Following device implantation, the burst phase of therapeutic release occurs. This phase is relatively short in duration and takes place when aqueous humor from the anterior chamber (or any other liquid such as interstitial fluid from ocular tissue) penetrates the pores of the matrix at the surfaces exposed to such liquid through the inlets. Therapeutic molecules (and any desired conjugates) embedded in the matrix near the matrix-aqueous interface diffuse out of the DRE and are released into the anterior chamber (or any other liquid such as interstitial fluid from ocular tissue) at a relatively high rate. Following the burst phase is a relatively longer period in which there exists an influx of aqueous humor (or any other liquid such as interstitial fluid from ocular tissue) into the core of the polymeric matrix. Polymeric crosslinks are cleaved at random locations due to hydrolysis or enzymes, creating larger pores, and resulting in an efflux of therapeutic molecules as well as any desired conjugates embedded in the core of the matrix at a near constant rate yet lower than that present in the burst phase. The third phase of delivery is at least as long as the previous and involves the biodegradation of the polymeric matrix. The biodegradation is a consequence of polymeric scission from the diffusion of aqueous humor (or any other liquid such as interstitial fluid from ocular tissue) into the matrix to the degree of physical instability. Much of the therapeutic has already effluxed out into the anterior chamber (or any other liquid such as interstitial fluid from ocular tissue), so the rate of osmotic influx of aqueous humor (or any other liquid such as interstitial fluid from ocular tissue) into the matrix is reduced. The result is a tapered release of a therapeutic and any desired conjugates from a structurally disturbed matrix. It is preferably during this tapered release stage that the device is explanted.

The biodegradable DRE can be composed of natural or synthetic materials. In some embodiments the biodegradable DRE may be composed of a material such as poly(lactic acid), poly(glycolic acid), poly(lactide-co-glycolide), poly(anhydrides), poly(dioxanone), poly(amides), poly(hydroxy butyrate), polyester, poly(caprolactone), poly(glycolide-co-lactide-co-caprolactone), poly(adepic acid), poly(sebacic acid), poly(terpthalic acid), poly(amino acids), poly(glutamic acid), poly(imino carbonate), poly(phosphates), poly(phosphonates), poly(phosphazenes), poly(cyanoacrylates), poly(urethanes), poly(ortho ester), poly(acetals), collagen, albumin, gelatin, alginate, cyclodextrin, chitosan, dextran, agarose, hyaluronic acid, starch, cellulose, and the like. In some embodiments, the biodegradable DRE may be composed of a combination of materials.

In some embodiments, a biodegradable DRE may consist of at least two heterogeneous biodegradable polymeric matrices. In such an embodiment the DRE is made up of at least two distinct strata; each strata comprising a homogeneous polymeric biodegradable matrix. There may exist different therapeutics and/or therapeutic concentrations within each stratum. Additionally, the therapeutics within each stratum may be intended to treat more than one systemic and/or ocular condition. Each stratum can be distinct with respect to the polymeric characteristics that make up their matrices, which include but are not limited to the type of polymer, stereoisomer composition, the sequence of monomeric units (e.g. block vs. alternating polymers), the orientation of monomeric units (e.g. chain vs. graft copolymers), and the monomer ratios of a certain polymer. Preferably, there exists a core matrix surrounded or coated with at least one other matrix of different character. Each successive surrounding matrix exists closer to the perimeter of the device and the final stratum is at least partially exposed to the environment. In one such embodiment a core matrix is surrounded by a second matrix that is at least partially exposed to the environment; both strata are composed of PLGA matrices with the inner matrix containing a lower PLA:PGA ratio and a higher concentration of a therapeutic and any desired conjugate for the sake of altering the pharmacokinetic curve.

In some embodiments, the polymer matrices in each respective stratum can be constructed via the crosslinking methods described above. Similarly, therapeutics can be combined with each matrix using previously described methods. The pore size of each homogeneous matrix will be contingent on the characteristics of the polymer that affect the crosslinking density, such as the length of its chains. Crosslinking densities will affect the rate of release and are preferably constant but may differ across the matrix. The concentration distribution of at least one therapeutic within each stratum's matrix is preferably monolithic, or constant. However, the concentration can possess a gradient across a stratum's matrix for the sake of achieving a preferred pharmacokinetic curve.

The matrix desired to degrade last can be formed into a gel with a preferred geometry through aforementioned methods and placed into the part of the DRE cavity most distant from the inlet(s) in the interior of the device. The matrix desired to degrade next can also be formed into a gel with a preferred geometry and placed in the DRE cavity adjacent to the previous and closer in distance to the inlet(s). This stepwise process continues until the matrix desired to degrade first is formed into a preferred geometry and placed into the DRE cavity where it can be exposed to aqueous humor (or any other liquid such as interstitial fluid from ocular tissue) via the inlets.

The three phases of therapeutic release will occur in the matter described above for the homogeneous polymeric matrices in each stratum. Preferably, the polymeric matrix nearer to the inlet will have experienced its burst release phase and zero-order release phase before the adjacent matrix begins its burst release phase. However, any three of the release phases in one matrix can occur simultaneously with any release phase of another. In other words, though the strata are physically separated, their stages of therapeutic release may not be. The duration of therapeutic release of each stratum will depend on the nature of the polymer used along with the geometries of the shaped matrix and inlet(s).

The following kinetics may pertain to an entire DRE or to a specific homogeneous biodegradable polymeric matrix stratum:

The in vivo aggregate drug release period referred to herein is defined as the time interval in which loaded therapeutics are distributed across at least one inlet. In other words, it begins with the initial release of at least one therapeutic into the surrounding environment and concludes via implant explantation or the cumulative release of all therapeutics incorporated. This release period may exist at least 1 hour, and up to 6 years, or longer.

The duration of implantation will last at least as long as the in vivo aggregate drug release period; however, the implant may remain in its designated ocular location to allow aqueous humor to egress from the anterior chamber 805 by way of the embedded channel or to limit a patient's surgical frequency, among other reasons.

In some embodiments the pharmacokinetic curve is altered by adjusting certain properties of the DRE such as, chemical structure, chemical composition, distribution of monomers in multimers, presence of ionic groups, presence of chain defects, particle shape, particle size, particle solubility, molecular weight distribution, presence of low-molecular weight compounds, polymer morphology (amorphous/semi crystalline, microstructures, and the like), therapeutic shape, therapeutic size, therapeutic solubility, therapeutic half-life, processing conditions, annealing, sterilization process, storage history, molecular weight, pH, shape, size, number of inlets, and the like.

In some embodiments, a biodegradable DRE may consist of at least one type of micro- or nanoparticle embedded in at least one polymeric matrix that maintains at least one therapeutic by way of encapsulation or conjugation. The particles may be coated with a biocompatible polymer or a biological ligand or modified at the surface for the sake of delivering to a specific location in the body or enhancing therapeutic effectiveness. Particles can encapsulate a therapeutic in solution; these include micro- or nanocapsules, liposomes, micelles, micro- or nanoemulsions, or a colloidal embodiment of the like. Alternatively, the particles can be monolithic and embed a therapeutic in a constant fashion, such as micro- or nanospheres or micro- or nanoscale lipid carriers. Alternatively, the particles can be polymeric or macromolecular carriers or excipients with a therapeutic attached; these include dendrimers and micro- or nanoconjugates. These therapeutic-containing particles can be manufactured using a method such as homogenization techniques, solvent emulsification/evaporation, W/O/W double emulsion techniques, spray drying, phase separation, precipitation, or conjugation techniques (e.g. grafting).

In some embodiments, the aforementioned particles are embedded within the pores of a homogenous biodegradable polymer matrix by mixing a biodegradable polymer or constituents of a polymer (monomer units and a possible initiator) in solution with at least one kind of particle in solution, then gelling or solidifying the mixture via application of at least one external stimulus, such as temperature or the like. Alternatively, a solid form of at least one type of particle can be incorporated into the pores of a polymeric matrix. In one such embodiment, the concentration distribution of at least one type of particle within a matrix is monolithic, or constant. In another such embodiment, the concentration can possess a gradient across a matrix for the sake of achieving a preferred pharmacokinetic curve.

In some embodiments, the particles embedded within a polymer matrix can release a therapeutic once an external stimulus has crossed a threshold. Certain stimuli can include but are not limited to temperature, pH, light intensity, electric field, and magnetic field. In one such embodiment, embedded particles consisting at least partially of thermosensitive poly(N-isopropylacrylamide) release at least one therapeutic upon crossing its lower critical solution temperature (LCST) inside the anterior chamber of the eye. In another such embodiment, particles consisting at least partially of a poloxamer release at least one therapeutic upon surpassing a unique LCST once inside the anterior chamber.

In some embodiments, the matrix can be formed into a gel with a preferred geometry through methods known in the art. The shaped gel may be placed into a DRE cavity in the interior of the device. In other embodiments, the nanoparticle/polymer mixture can be delivered into the cavity in the interior of the implant in solution form and the polymer subsequently cross-linked or solidified.

The three phases described above with respect to therapeutic release hold true for nanoparticle release as well. The size of a micro- or nanoparticle is an additional factor in determining its release kinetics. Once released from the matrix, the micro- or nanoparticle will exist in the anterior chamber of the eye (or within any other ocular tissue) and may be transported to a targeted ocular location before releasing a therapeutic. Release of a therapeutic from a micro- or nanoparticle can occur via a number of different methods, which include but are not limited to diffusion of a therapeutic from the micro- or nanoparticle and biodegradation of a micro- or nanoparticle through lysis by way of a biochemical reaction, such as hydrolysis. A therapeutic may be effective at the site of release from a particle or may be further transported to an intended location within or external to the eye.

In some embodiments, the intended target for drug delivery is not local to the eye. In such embodiments, the therapeutic delivered is intended for systemic effects or intended for a location outside of the eye.

In some embodiments there can exist more than one kind of therapeutic in each type of particle. Additionally, there can exist more than one type of particle within the homogeneous polymeric matrix that constitutes each stratum. Furthermore, as discussed above, multiple particle-containing heterogeneous matrices can be patterned alongside each other in a DRE cavity.

In some embodiments, an osmotic pressure is generated inside the DRE by way of a semipermeable membrane that is placed in fluid contact with the anterior chamber 805 (or any other compartment that contains liquid such as interstitial fluid from ocular tissue) abutting the DRE. This type of DRE does not contain a direct inlet to the anterior chamber, but rather builds pressure by selectively allowing water to enter the DRE through the semipermeable membrane. The pressure is relieved as therapeutic flows out of the DRE through the semipermeable membrane. The rate of efflux in this case can be controlled by the size of the semipermeable membrane/DRE interface.

What is claimed is:

1. An implantable ocular drug delivery device, comprising:
    a body comprising:
        a top outer polymer layer;
        a bottom outer polymer layer; and
        an inner polymer layer disposed between the top and bottom outer polymer layers and defining a reservoir and an inlet to the reservoir,
        wherein the body includes a distal end portion and a proximal end portion, wherein the proximal end portion includes a crossbar tab that is a laterally wider than the distal end portion of the device; and
    a drug releasing entity comprising a therapeutic agent, the drug releasing entity disposed within the reservoir defined by the inner polymer layer,
    wherein the device is configured to be implanted through scleral tissue of an eye such that at least a distal end portion of the device is within an anterior chamber of the eye and the crossbar tab abuts an outer surface of the eye.

2. The device of claim 1, wherein the top and bottom outer polymer layers comprise thermoplastic polyurethane.

3. The device of claim 1, wherein the first and second outer polymer layers comprise polyethylene terephthalate ("PET"), Poly(methyl methacrylate) ("PMMA"), Polyurethane ("PU"), Polycarbonate ("PC"), Polyvinyl chloride ("PVC"), Polyvinyl alcohol ("PVA"), Polystyrene ("PS"), Thermoplastic polyurethane ("TPU"), Polyethylene ("PE"), Polysulfone, Polyethersulfone ("PES"), Sulfonated Polyethersulfone ("SPES"), Polybutylene terephthalate ("PBT"), Polyhydroxyalkanoates ("PHAs"), Silicone, Parylene, Polypropylene ("PP"), Fluoropolymers, Polyhydroxylethylmethacrylate ("pHEMA"), Polyetherketoneketone ("PEKK"), Polyether ether ketone ("PEEK"), Polyaryletherketone ("PAEK"), Poly(lactic-co-glycolic acid) ("PLGA"), Polytetrafluoroethylene ("PTFE"), Polyvinylidene fluoride ("PVDF"), or Polyacrylic acid ("PAA").

4. The device of claim 1, wherein the therapeutic agent is formulated to treat an ocular disease or ocular condition.

5. The device of claim 1, wherein the therapeutic agent is formulated to treat a disease or condition outside of the eye.

6. The device of claim 1, wherein the drug releasing entity comprises a polymeric matrix that includes poly(lactic acid), poly(glycolic acid), poly(lactide-co-glycolide), poly(anhydrides), poly(dioxanone), poly(amides), poly(hydroxy butyrate), polyester, poly(caprolactone), poly(adepic acid), poly(sebacic acid), poly(terpthalic acid), poly(amino acids), poly(glutamic acid), poly(imino carbonate), poly(phosphates), poly(phosphonates), poly(phosphazenes), poly(cyanoacrylates), poly(urethanes), poly(ortho ester), poly(acetals), poly(dimethylsiloxane), poly(urethane), poly(amido amines), poly(amide-enamines), poly(acrylates), poly(acrylamides), poly(carbophil), poly(acrylic acid), poly(ethylene-vinyl acetate), poly(vinyl alcohol), poly(enol-ketone), poly(ethylene), poly(propylene), poly(vinyl chloride), poly(ortho esters), poly(ether-ester), collagen, albumin, gelatin, alginate, cyclodextrin, chitosan, dextran, agarose, hyaluronic acid, starch, or cellulose.

7. The device of claim 1, wherein the inner polymer layer comprises an anti-biofouling polymer.

8. The device of claim 1, wherein the inner polymer layer comprises polyethylene glycol ("PEG") (e.g., an acrylate-PEG-acrylate such as triethylene glycol dimethacrylate), a polymerized zwitterion, N-(2-methacryloyloxy)ethyl-N, N-dimethylammonio propanesulfonate ("SPE"), N-(3-methacryloylimino)propyl-N, N-dimethylammonio propanesulfonate ("SPP"), 2-(methacryloyloxy)ethylphosphatidylcholine ("MPC"), 3-(2'-vinyl-pyridinio)propanesulfonate ("SPV")), Poly(2-oxazoline)s (e.g. Poly(2-ethyl-2-oxazoline)), Poly(hydroxyfunctional acrylates) (e.g. Poly(2-hydroxyethyl methacrylate); Poly(glycerol)), poly(vinylpyrrolidone), peptides or peptoids (e.g. Poly(amino acid) or Poly(peptoid)).

9. The device of claim 1, wherein the drug releasing entity contains the therapeutic agent and one or more of group consisting of: release enhancers, release-hindering agents, buffering agents, prodrugs, drug preservatives, diluents, and drug carriers.

10. The device of claim 1, wherein the drug releasing entity is nonbiodegradable.

11. The device of claim 1, wherein the device has a length between about 2 mm and 4 mm, a width between about 0.5 mm and 2 mm, and a height between around 0.1 mm and 0.5 mm.

12. The device of claim 1, wherein a microchannel through the device is defined by the inner polymer layer and runs through the device along its length.

13. The device of claim 12, wherein the microchannel is configured to reduce an intraocular pressure of the eye after implantation.

14. The device of claim 12, wherein the microchannel is configured to treat dry eye.

15. The device of claim 1, wherein the therapeutic agent is a first therapeutic agent, wherein the drug releasing entity further comprises a second therapeutic pharmacological agent, and wherein the first and second therapeutic agents are different types of therapeutic agents.

16. The device of claim 1, wherein the drug releasing entity is exposed to aqueous humor via the inlet when the device is implanted within scleral tissue of an eye such that at least the distal end portion of the device is within an anterior chamber of the eye.

17. The device of claim 1, wherein the reservoir is a first reservoir, and wherein the inner polymer also defines a second reservoir.

18. The device of claim 17, wherein the first reservoir stems from a first inlet and the second reservoir stems from a second inlet, wherein the first and second inlets are within the anterior chamber of the eye while the device in implanted within the scleral tissue of the eye, and wherein other than the first and second inlets the remainder of the device is impermeable to aqueous fluids.

19. The device of claim 1, wherein the crossbar tab has rounded corners.

* * * * *